(12) United States Patent
Schoonmaker et al.

(10) Patent No.: US 10,434,285 B2
(45) Date of Patent: Oct. 8, 2019

(54) SELF-CONTAINED INSERTER FOR DRUG DELIVERY INFUSION SET

(75) Inventors: Ryan Schoonmaker, San Marcos, CA (US); Cole Constantineau, Cambridge, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 52 days.

(21) Appl. No.: 13/984,009

(22) PCT Filed: Feb. 8, 2012

(86) PCT No.: PCT/US2012/000073
§ 371 (c)(1),
(2), (4) Date: Oct. 31, 2013

(87) PCT Pub. No.: WO2012/108958
PCT Pub. Date: Aug. 16, 2012

(65) Prior Publication Data
US 2014/0058360 A1    Feb. 27, 2014

Related U.S. Application Data

(60) Provisional application No. 61/441,201, filed on Feb. 9, 2011.

(51) Int. Cl.
*A61M 25/06* (2006.01)
*A61M 5/158* (2006.01)
*A61M 5/142* (2006.01)

(52) U.S. Cl.
CPC ........ *A61M 25/0606* (2013.01); *A61M 5/158* (2013.01); *A61M 2005/14252* (2013.01);
(Continued)

(58) Field of Classification Search
CPC .......... A61M 5/158; A61M 2005/1581; A61M 2005/1585; A61M 2005/1586;
(Continued)

(56) References Cited

U.S. PATENT DOCUMENTS 7,128,727 B2    10/2006    Flaherty et al.
2002/0022855 A1    2/2002    Bobroff et al.
(Continued)

FOREIGN PATENT DOCUMENTS

EP          1820525 A1      8/2007
JP          2008528087 A    7/2008
WO       WO-2012108959 A1  8/2012

*Primary Examiner* — Nathan R Price
*Assistant Examiner* — Justin L Zamory
(74) *Attorney, Agent, or Firm* — Dickinson Wright PLLC (57) ABSTRACT

An infusion set (101) includes a base (121), a flexible catheter (142) and an introducer needle (134). The flexible catheter (142) is movable from a first catheter position disposed substantially entirely within the base (121) to a second catheter position in which a free end of the flexible catheter (142) is disposed externally of the base (121). The introducer needle (134) is movable between a first introducer needle position disposed substantially entirely within the base (121) and a second introducer needle position in which a free end of the introducer needle (134) is disposed externally of the base (121). An activation button (161) is movable between first and second button positions. When the activation button (161) is moved from the first button position to the second button position, the flexible catheter (142) is moved from the first to the second catheter position, and the introducer needle (134) is moved from the first to the second introducer needle position to facilitate insertion of the catheter (142) and back to the first introducer needle position to store the introducer needle (134) within the base (121).

23 Claims, 7 Drawing Sheets

(52) U.S. Cl.
CPC .......... *A61M 2005/14284* (2013.01); *A61M 2005/1585* (2013.01)

(58) Field of Classification Search
CPC .......... A61M 2005/1587; A61M 25/00; A61M 25/06; A61M 25/0606
USPC ...... 604/93.01, 158, 164.01, 164.04, 164.07, 604/180, 510, 164.08, 500, 506, 507, 508, 604/509
See application file for complete search history.

(56) References Cited

U.S. PATENT DOCUMENTS

| | | | |
|---|---|---|---|
| 2002/0123740 A1* | 9/2002 | Flaherty | A61M 5/14248 604/890.1 |
| 2004/0158207 A1* | 8/2004 | Hunn | A61M 5/158 604/164.01 |
| 2005/0203461 A1* | 9/2005 | Flaherty | A61M 5/14248 604/131 |
| 2006/0282290 A1 | 12/2006 | Flaherty et al. | |
| 2007/0093754 A1 | 4/2007 | Mogensen et al. | |
| 2007/0191772 A1 | 8/2007 | Wojcik | |
| 2009/0012472 A1 | 1/2009 | Ahm et al. | |
| 2009/0254041 A1* | 10/2009 | Krag et al. | 604/180 |

* cited by examiner

SELF-CONTAINED INSERTER FOR DRUG DELIVERY INFUSION SET

CROSS REFERENCE TO RELATED APPLICATION

This application claims the benefit under 35 U.S.C. § 119(e) of U.S. Provisional Application Ser. No. 61/441,201, filed Feb. 9, 2011, which is hereby incorporated by reference in its entirety.

FIELD OF THE INVENTION

The present invention relates generally to an infusion set having a self-contained inserter. More particularly, the present invention relates to a self-contained inserter in which an introducer needle is stored in a base after being withdrawn from an insertion site. Still more particularly, the present invention relates to a self-contained inserter in which an introducer needle and catheter are inserted at an insertion site and the introducer needle is withdrawn from the insertion site by the push of a button.

BACKGROUND OF THE INVENTION

A large number of people, including those suffering from conditions such as diabetes, use some form of infusion therapy, such as daily insulin infusions, to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. Infusion pumps, although more complex than syringes and pens, offer the advantages of continuous infusion of insulin, precision dosing and programmable delivery schedules. This results in closer blood glucose control and an improved feeling of wellness.

The use of an infusion pump further requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive that retains the base on the skin surface during use. The hub or base may be applied to the skin manually or with the aid of a manual or automatic insertion device. Often, the insertion device is a separate, stand-alone unit that the user is required to carry and provide.

There are many available versions of infusion sets, including steel cannula infusion sets and soft (flexible) catheter sets. Soft catheter sets are typically inserted into a patient manually with the aid of a steel introducer needle, which is later removed from the patient leaving the soft catheter in place. In another type of infusion set, as noted above, a mechanized inserter is used to insert the introducer needle and catheter, remove the introducer needle, or both. The introducer needle is completely removed from the infusion set before being connected to the insulin pump.

One problem associated with manually inserting and retracting the introducer needle is variability in the insertion and retraction force, speed, smoothness and angle. This variability can lead to an increased rate of catheter insertion failure.

Further, as noted above, the user typically must remove the introducer needle after inserting the cannula. This exposes the user to accidental needle sticks from handling the removed introducer needle.

Accordingly, a need exists for an infusion set that facilitates insertion of the cannula, while reducing the number of components a user must carry and substantially preventing accidental introducer needle sticks.

SUMMARY OF THE INVENTION

An object of the present invention is to provide an exemplary infusion set that includes an integral introducer needle to facilitate cannula insertion.

Another object of the present invention is to provide an infusion set having an integral self-contained introducer needle to facilitate cannula insertion and reduce the number of components a user must carry.

Another object of the present invention is to provide an infusion set in which insertion of the catheter and introducer needle and retraction of the introducer needle is automatic, thereby substantially eliminating variability from the process.

Another object of the present invention is to provide an infusion set having an integrated self-contained introducer needle to substantially reduce the overall size of the infusion set.

In accordance with exemplary embodiments of the present invention, a drug delivery infusion set houses and stores an introducer needle and the means to insert and retract the introducer needle. The catheter and introducer needle are self-contained within the base of the infusion set. The introducer needle is automatically and fully retracted within the self-contained inserter. Because the introducer needle is self-contained in the base of the infusion set, the user does not have to manually remove the introducer needle. Thus, user contact with the introducer needle is avoided, thereby preventing accidental introducer needle sticks.

An infusion set in accordance with exemplary embodiments of the present invention includes a base, a catheter and an introducer needle. The catheter is movable from a first catheter position disposed substantially entirely within the base to a second catheter position in which a free end of the catheter is disposed externally of the base. The introducer needle is movable between a first introducer needle position disposed substantially entirely within the base and a second introducer needle position in which a free end of the introducer needle is disposed externally of the base. An activation button is movable between first and second button positions. When the activation button is moved from the first button position to the second button position, the catheter is moved from the first to the second catheter position, and the introducer needle is moved from the first to the second introducer needle position to facilitate insertion of the catheter and back to the first introducer needle position to remove the introducer needle. Accordingly, the introducer needle is stored within the base of the infusion set to prevent accidental introducer needle sticks.

As used in this application, the terms "front," "rear," "upper," "lower," "upwardly," "downwardly," and other orientational descriptors are intended to facilitate the description of the exemplary embodiments of the present invention, and are not intended to limit the structure thereof to any particular position or orientation.

BRIEF DESCRIPTION OF THE DRAWINGS

The various objects, advantages and salient features of the present invention will become more apparent from the following detailed description of exemplary embodiments thereof and from the accompanying drawing figures, in which.

Throughout the drawings, like reference numerals will be understood to refer to like parts, components and structures.

DETAILED DESCRIPTION OF THE EXEMPLARY EMBODIMENTS

The exemplary embodiments of the present invention described below provide a novel means of inserting an infusion catheter into the skin. For example, exemplary embodiments of the present invention provide an integrated and self-contained inserter that inserts the catheter into the skin and withdraws the introducer needle into a base of an infusion set, as shown in FIGS. 1-14, thereby providing a low profile infusion set.

Figure 1:
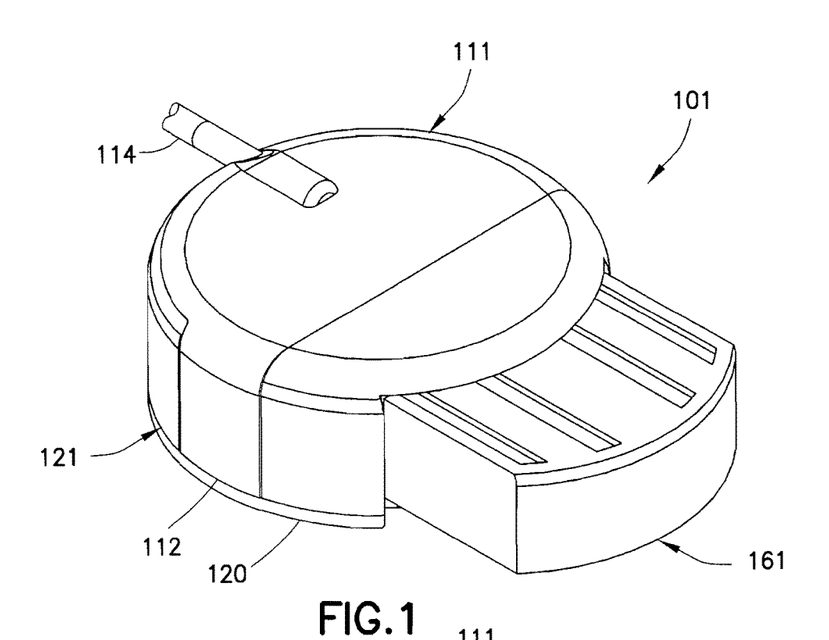
FIG. 1 is a perspective view of an assembled infusion set in accordance with an exemplary embodiment of the present invention, with an activation button shown in a first position.
Figure 2:
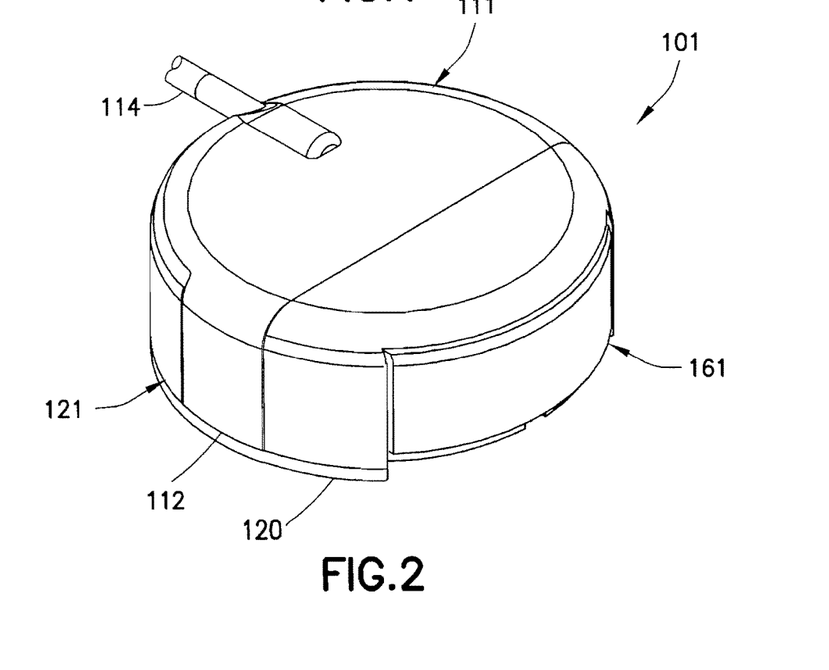
FIG. 2 is a perspective view of the assembled infusion set of FIG. 1, with the activation button in a second position.

A base 121 of an infusion set 101, as shown in FIGS. 1 and 2, is preferably provided with a skin-securing, adhesive layer 120 to secure the infusion set to the skin surface at a desired catheter insertion site. The adhesive layer 120 ensures that the base 121 is at the proper position relative to the skin surface, and that the skin is secured during insertion to further aid introducer needle insertion with a reduced risk of tenting of the skin surface. For clarity, the adhesive layer 120 is shown only in FIGS. 1 and 2, and is omitted from the remaining drawing figures.

Figure 8:
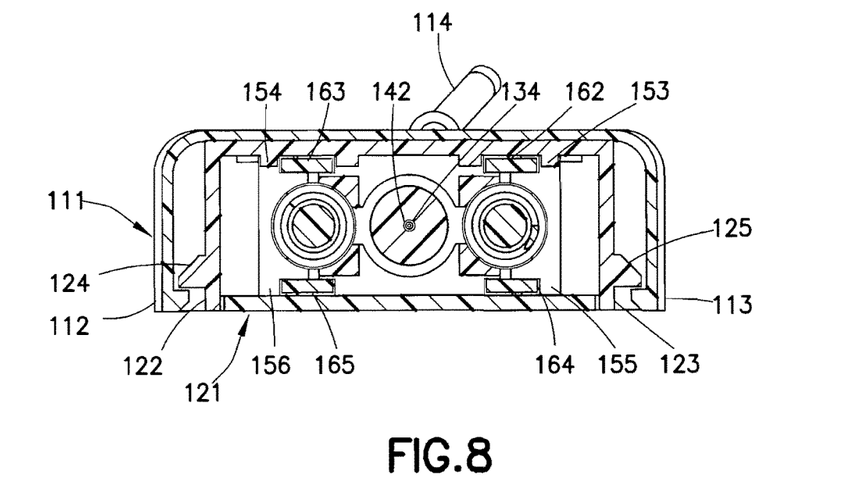
FIG. 8 is an elevational view in cross-section of the activation button of the infusion set of FIG. 1.

The base 121 has a first recess 122 and a second recess 123 adapted to receive first and second tabs 112 and 113 of a fluid connector 111, thereby securing the fluid connector 111 to the base 121 to fully assembly the infusion set 101, as shown in FIGS. 1 and 8. First and second ramped surfaces 124 and 125 slope outwardly toward the first and second recesses 122 and 123, respectively. The fluid connector tabs 112 and 113 slide down the ramped surfaces 124 and 125 into the first and second recesses 122 and 123, thereby creating a snap-fit connection. Flexing the fluid connector tabs 112 and 113 outwardly away from the base 121 allows the fluid connector 111 to be disconnected from the base 121.

Figure 3:
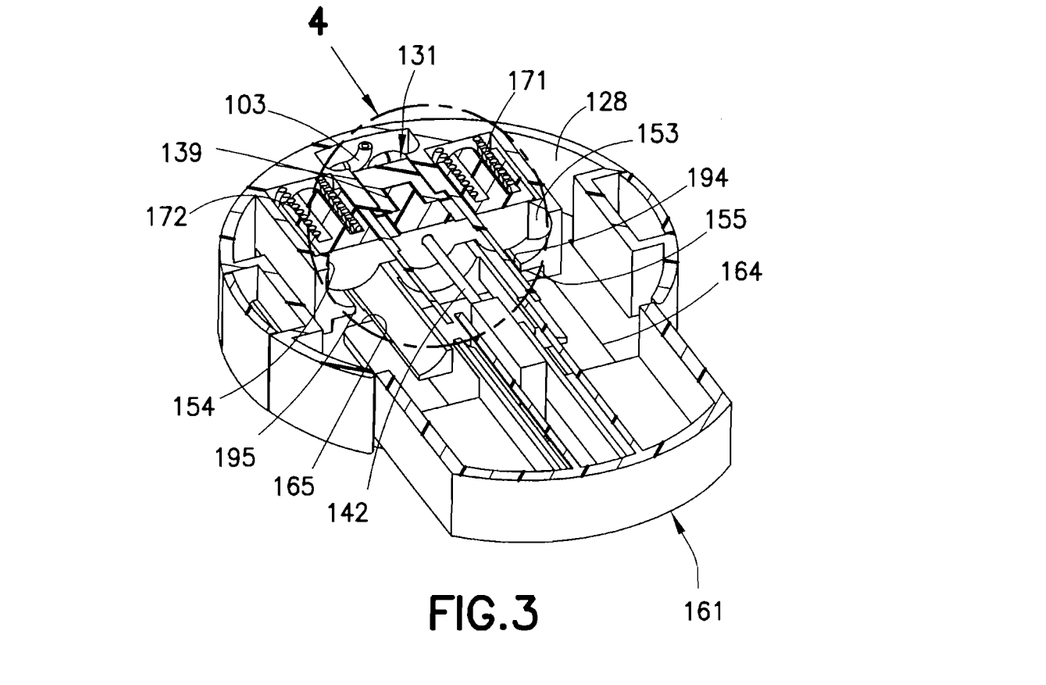
FIG. 3 is a partial perspective view in cross-section of the base of the infusion set of FIG. 1.
Figure 4:
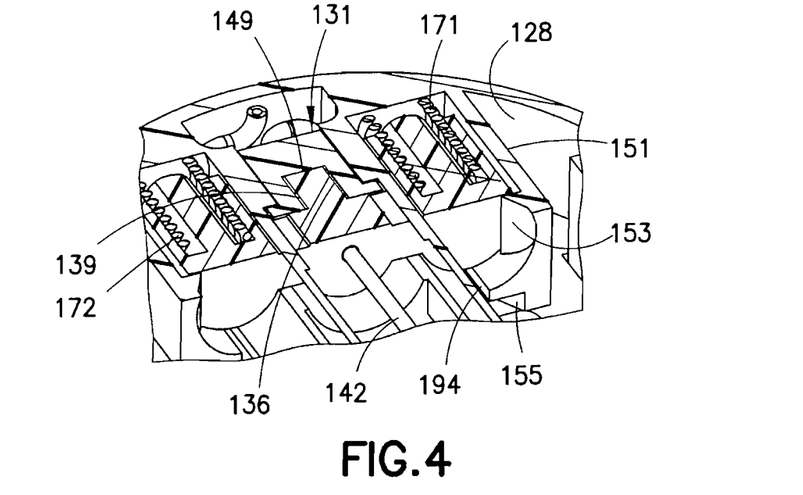
FIG. 4 is an enlarged perspective view in cross-section of the catheter hub and spring members of FIG. 3.
Figure 5:
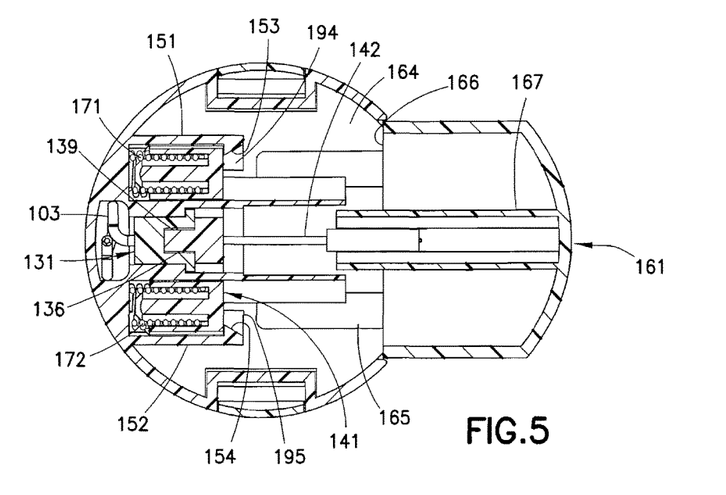
FIG. 5 is a top plan view in cross-section of the base of FIG. 3.

First and second flexible members 151 and 152 extend inwardly from a wall 128 of the base 121, as shown in FIGS. 3 and 5. Each flexible member 151 has upper chamfered portions 153 and 154 and lower chamfered portions 155 and 156, as shown in FIGS. 3 and 8. As shown in FIGS. 3-5, the chamfered portions of the flexible members 151 and 152 receive an introducer hub 131 and a catheter hub 141.

Figure 9:
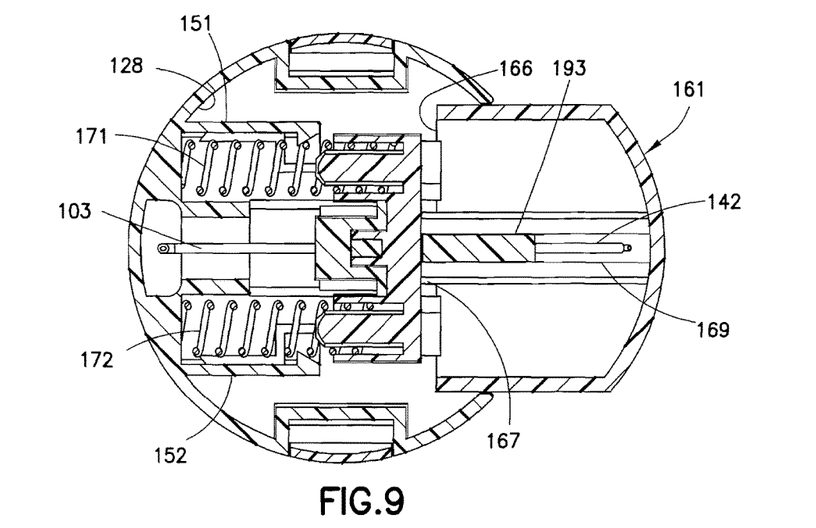
FIG. 9 is a top plan view in cross-section of the activation button releasing the spring members in the infusion set of FIG. 1.

First and second spring members 171 and 172 are disposed between the base wall 128 and the catheter hub 141, as shown in FIGS. 3-5. Preferably, the first and second spring members 171 and 172 are compression springs. When the flexible members 151 and 152 retain the introducer hub 131 and the catheter hub 141, the spring members 171 and 172 are in a loaded position. When the flexible members 151 and 152 are flexed outwardly, the compressed spring members 171 and 172 are released and drive the introducer hub 131 and catheter hub 141 outwardly, as shown in FIGS. 9 and 10.

Figure 10:
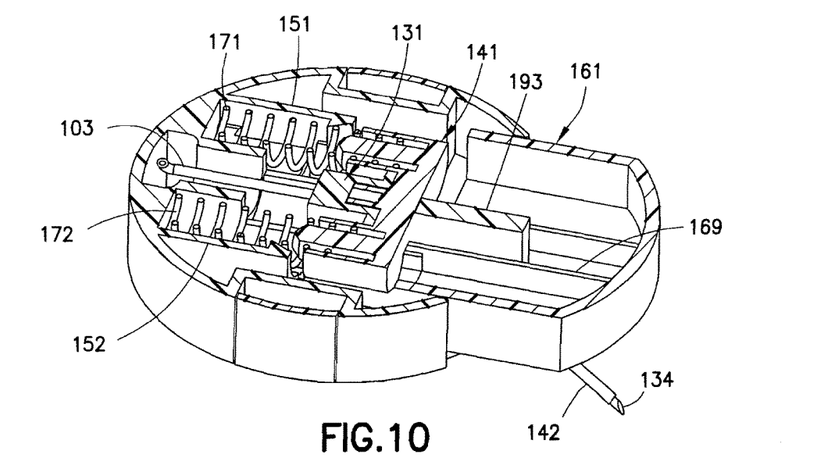
FIG. 10 is a perspective view in cross-section of the activation button releasing the spring members of FIG. 9.
Figure 11:
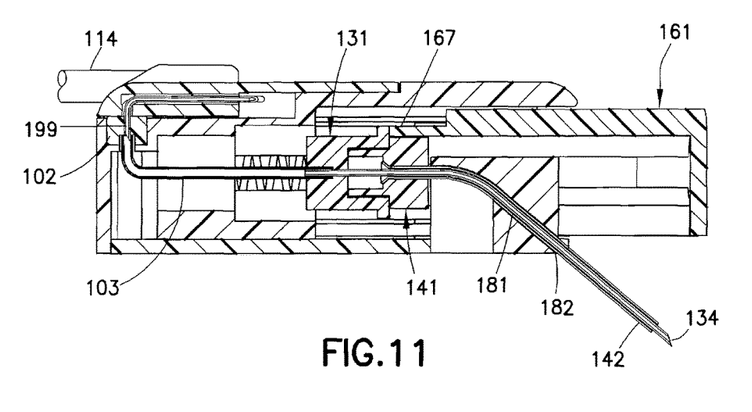
FIG. 11 is an elevational view in cross-section of the introducer needle and catheter of FIGS. 9 and 10 in their inserted positions.

The introducer hub 131 is movably disposed in the base 121 of the infusion set 101, as shown in FIGS. 3 and 10. Preferably, the introducer hub 131 is substantially cylindrical with a flange 132 extending outwardly at one end thereof. An opening 133 is formed in the opposite end of the introducer hub 131 and receives an end of tubing 103. A hollow, bendable introducer needle 134 is rigidly fixed to the introducer hub 131, such that movement of the introducer needle is controlled by movement of the introducer hub 131.

Figure 12:
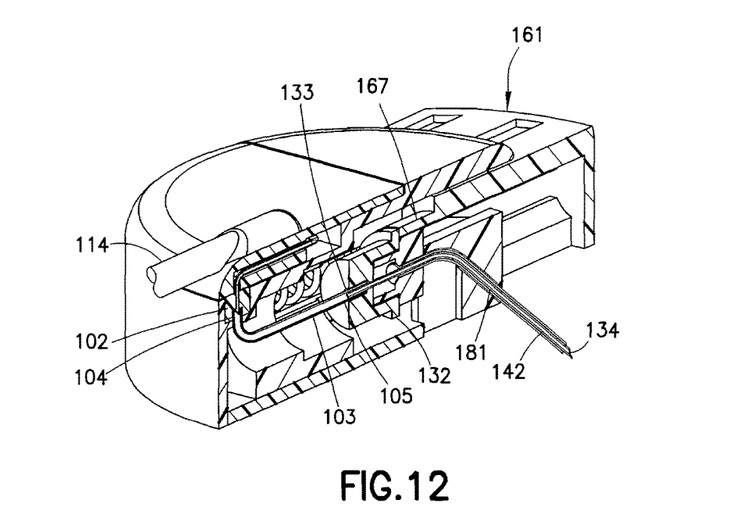
FIG. 12 is a perspective view in cross-section of the inserted introducer needle and catheter of FIG. 11.
Figure 13:
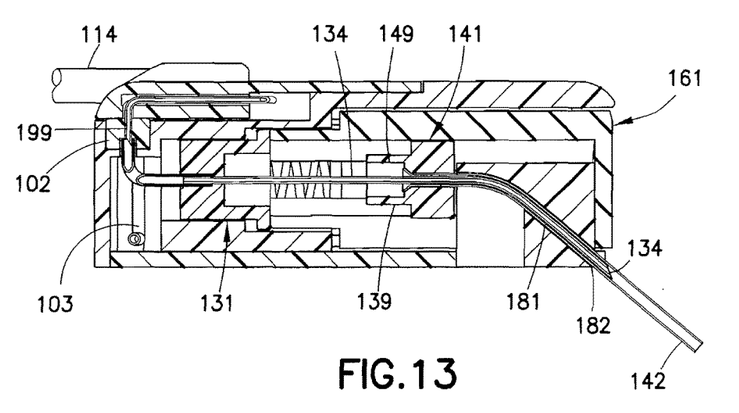
FIG. 13 is a perspective view in cross-section of the introducer needle of FIG. 12 in a retracted position.
Figure 14:
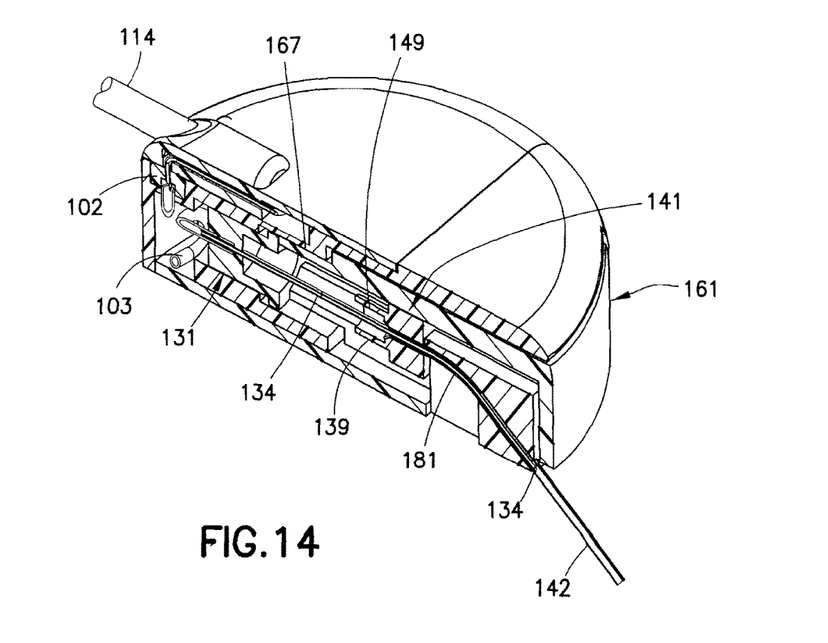
FIG. 14 is another perspective view in cross-section of the introducer needle of FIG. 12 in its retracted position.

The introducer hub 131 is movable from a first position shown in FIGS. 3-5, to a second position shown in FIGS. 9-12, and back to the first position shown in FIGS. 13 and 14. When the introducer hub 131 is in the first position, the introducer needle 134 is disposed substantially entirely within the base 121, thereby preventing accidental introducer needle sticks. When the introducer hub 131 is in the second position, a free end of the introducer needle 134 is exposed outside of the base 121 such that a patient's skin can be pierced to insert a flexible catheter 142.

The tubing 103 is disposed in the base 121 and has a first end 104 disposed in the septum 102 and a second end 105 connected to the introducer hub opening 133, as shown in FIG. 12. The tubing 103 is initially in a coiled configuration, as shown in FIG. 5. The tubing 103 moves with linear movement of the introducer hub 131 to a straight configuration as shown in FIG. 9. The tubing 103 returns to the coiled configuration of FIG. 5 when the introducer hub 131 is returned to its initial position when retracting the introducer needle 134, as shown in FIGS. 13 and 14.

The catheter hub 141 initially abuts the introducer hub 131, as shown in FIGS. 3-5. The flexible catheter 142 is rigidly connected to the catheter hub 141. The introducer needle 134 is movably disposed within the catheter 142, as shown in FIGS. 11-14. Linear movement of the catheter hub 141 results in linear movement of the introducer hub 131 because of the engagement between an annular projection 139 of the catheter hub 141 and a corresponding recess 136 in the introducer hub 131. The catheter hub 141 is movable between a first position as shown in FIGS. 3-5, and a second position as shown in FIGS. 11-14. When the catheter hub 141 is in the first position, the flexible catheter 142 is substantially entirely disposed within the base 121. When the catheter hub 141 is moved to the second position, the catheter 142 is moved out of the base 121 such that a free end of the catheter 142 is disposed externally of the base 121 and is insertable at an angle under the surface of the patient's skin. The introducer hub 131 is movable between a first position shown in FIGS. 3-5 in which the introducer needle 134 is stored within the base 121, a second position shown in FIGS. 11 and 12 in which the introducer needle 134 is moved out of the base 121 and is insertable at an angle under the surface of the patient's skin, and back to the first position shown in FIGS. 13 and 14 in which the introducer needle 134 is extracted from the insertion site and withdrawn into the base 121 to prevent accidental sticks.

A septum 149 is disposed within the annular projection 139 of the catheter hub 141, as shown in FIGS. 4, 13 and 14. The hollow introducer needle 134 maintains the fluid path between the introducer hub 131 in the first position and the catheter hub 141 in the second position as shown in FIGS. 13 and 14. The introducer needle 134 pierces the septum 149 disposed in the catheter hub 141 and has an end within the catheter 142. The other end of the introducer needle 134 is connected to the tubing 103.

An activation button 161 is movable between a first, or "out", position as shown in FIG. 1, and a second, or "in", position as shown in FIG. 2. A plurality of arms 162-165 extend outwardly from a front end 166 of the activation button 161, as shown in FIGS. 3 and 5-8. When the activation button 161 is in the first position, as shown in FIG. 5, the ends of the arms 162-165 are spaced from the hooks. When the activation button 161 is pressed inwardly to the second position, as shown in FIGS. 13 and 14, the button arms 162-165 engage and flex the hooks outwardly, thereby allowing the spring members to drive the introducer hub and catheter hub outwardly.

An angled guide 181 is provided in the base 121 to guide movement of the introducer needle 134 and the catheter 142, as shown in FIGS. 11-14. An opening 182 is formed in the base 121 at the end of the angled guide 181 to allow the introducer needle 134 and catheter 142 to exit the base. The angled guide 181 creates an angle with respect to the surface of the skin of between approximately 30 and 60 degrees, inclusive, and preferably about 45 degrees.

A septum 102 is disposed in the base 121, as shown in FIGS. 11-14. Preferably, the septum 102 has a slit to facilitate receiving a penetrating member, or sharp, 199 of the fluid connector 111, although the slit may not be required in some cases. The tubing 103 has a first end connected to the septum 102 and a second end connected to the introducer needle 134. The tubing 103 allows the introducer hub 131 to move from the first position to the second position and back to the first position while maintaining a fluid path with the tubing 114.

The fluid connector 111 has first and second flexible arms 112 and 113, as shown in FIGS. 1-3, that engage the first and second recesses 122 in the base 121 to secure the connector to the base. Tubing 114 extends from the fluid connector 111 and is adapted to connect to a pump, such as an insulin pump (not shown). The tubing 114 is connected to the penetrating member 199 extending downwardly from the connector 111, and a fluid path is formed therebetween. The penetrating member 199 is adapted to penetrate the septum 102 when the fluid connector 111 is connected to the base 121, as shown in FIGS. 11-14.

ASSEMBLY AND OPERATION

FIG. 1 is a perspective view of the infusion set 101 ready to be inserted by a user. The fluid connector 111 is secured to the base 121 by engaging the hooks of arms 112 and 113 in the base recesses 122, as shown in FIGS. 1, 2 and 8. Ramped surfaces 124 and 125 on the base 121 facilitate engaging the fluid connector arms 112 and 113 with the base recesses 122. The infusion set 101 can be supplied to the user with the fluid connector 111 pre-attached to the base 121, as shown in FIGS. 1 and 2.

An adhesive backing (not shown) is removed from the base 121 to expose the adhesive layer 120 on the lower surface of the base 121, such that the base can be firmly secured to a desired location on the skin.

The activation button 161 is initially in the out, or first, position, as shown in FIG. 1. In this position, the spring members 171 and 172 are compressed between the catheter hub 141 and the wall 128 of the base 121, as shown in FIGS. 3-5. The catheter hub 141 is prevented from moving linearly by the blocking portions 194 and 195 disposed between the chamfered portions 153-156 of the first and second flexible members, as shown in FIGS. 3-5. The first blocking portion 194 is disposed between chamfered portions 153 and 155, and the second blocking portion 195 is disposed between chamfered portions 154 and 156. The introducer hub 131 is disposed between the catheter hub 141 and the base wall 128, and is prevented from moving linearly by the catheter hub 141. An annular projection 139 on the catheter hub 141 receives the introducer hub 131, as shown in FIGS. 3-5, to allow the introducer hub 131 to move with the catheter hub 141. Preferably, the introducer hub 131 is passively connected to the catheter hub annular projection 139, such as by a snap-fit or other suitable means of attachment. The flexible catheter 142 and the introducer needle 134 are disposed within the base 121, thereby substantially preventing accidental introducer needle sticks.

To insert the catheter 142, the activation button 161 is pushed inwardly to an in, or second, position to release the compressed first and second spring members 171 and 172, thereby driving linear movement of the introducer hub 131 and the catheter hub 141.

Figure 6:
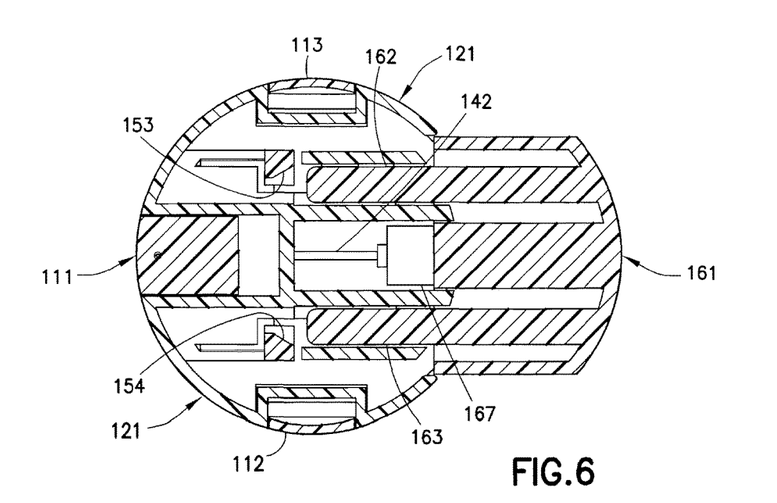
FIG. 6 is a top plan view in cross-section of the activation button engaging snap arms of the infusion set of FIG. 1.
Figure 7:
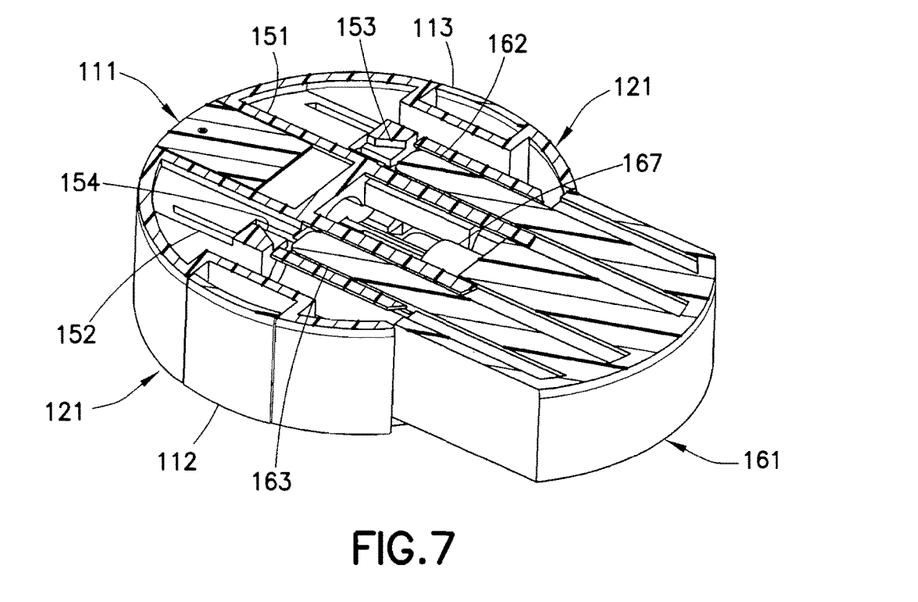
FIG. 7 is a perspective view in cross-section of the activation button and snap arms of FIG. 6.

As the activation button 161 begins to move inwardly, the button arms 162-165 move linearly toward the chamfered portions 153-156 of the first and second flexible members 151 and 152, as shown in FIGS. 6 and 7. When the activation button arms 162-165 engage the chamfered portions 153-156 of the first and second flexible members 151 and 152, the first and second flexible members 151 and 152 flex outwardly such that the compressed first and second spring members 171 and 172 are released. The first and second blocking portions 194 and 195 move out of engagement with the catheter hub 141 when the first and second flexible members 151 and 152 flex outwardly, thereby releasing the compressed first and second spring members 171 and 172. The stored energy in the compressed first and second spring members 171 and 172 drives the catheter hub 141 away from the first and second flexible members 151 and 152, as shown in FIGS. 9 and 10. The tubing 103 disposed between the septum 102 and the introducer hub 131 is moved to the stretched position, as shown in FIGS. 9 and 10. The flexible catheter 142 is fixedly attached to the catheter hub 141 and the introducer needle 134 is fixedly attached to the introducer hub 131. The angled guide 181 in the base 121 guides the downwardly angled movement of the flexible catheter 142 and introducer needle 134. The introducer needle 134 extends beyond the flexible catheter 142 such that the introducer needle 134 pierces the surface of the skin to allow the flexible catheter to be inserted at an angle beneath the surface of the skin. A stop member 193 disposed in the base 121 is abutted by the catheter member 141 to prevent further linear movement of the catheter hub 141 and the introducer hub 131. A groove 169 disposed in the activation button 161 receives the stop member 193 and allows the activation button 161 to be pushed past the stop member 193. The first and second spring members 171 and 172, which are now partially expanded but still under some compression, retain the catheter hub 141 in a position abutting the stop member 193 and substantially prevent movement of the catheter hub 141 back to its initial position, thereby maintaining the flexible catheter 142 in its inserted position. Alternatively, any other suitable means can be used to secure the catheter hub 141 in the position abutting the stop member 193, such as a snap connection.

As the activation button 161 continues to be pushed inwardly toward a third position, a projection 167 extending outwardly therefrom engages the introducer hub 131. The continued inward movement of the activation button 161 pushes the introducer hub 131 back to its initial position, as shown in FIGS. 13 and 14. The introducer huh 131 being returned to it, initial position withdraws the introducer needle 134 from the insertion site such that the introducer needle 134 is retracted completely into the base 121, leaving the flexible catheter 142 inserted at an angle beneath the surface of the skin. The activation button 161, in the third position, is flush with the base 121 of the infusion set 101, as shown in FIG. 14. The infusion set 101 is now ready to begin infusing insulin.

A fluid path is created from the connector tubing 114, through the septum 102, through the tubing 103, through the hollow introducer needle 134 and through the flexible catheter 142, as shown in FIGS. 13 and 14.

As described above, pushing the activation button 161 inwardly, from the first button position to the second button position and to the third button position in the same direction, causes both the insertion and retraction of the introducer needle 134. The forward movement of the introducer hub 131 to insert the introducer needle 134 is caused by the button arms 162-165 releasing the compressed first and second spring members 171 and 172 in the second button position. The introducer needle 134 is retracted by continued inward movement of the activation button 161 toward the third button position, which engages and pushes the introducer hub 131 back to its initial position as shown in FIGS. 13 and 14. By using a flexible or bending introducer needle 134 and an angled catheter 142, the infusion set can have a low profile. The angled guide 181 in the base 121 guides the introducer needle 134 downwardly into the surface of the skin. The only action required by the user is to press the activation button 161 inwardly. The insertion of the introducer needle 134 and the flexible catheter 142 and the retraction of the introducer needle 134 occurs automatically. By only requiring the user to push the activation button 161 inwardly, the infusion set 101 can be positioned and used in hard-to-reach and awkward body locations.

Embodiments of the present invention are usable for either intradermal or subcutaneous injections. A different method of maintaining the fluid connection is possible other than through the tubing 103 and delivery through the introducer needle 134. For example, a sliding gasket seal can be used between the septum 102 and the introducer hub 131, or any other suitable means of maintaining the fluid path. Alternative methods may be used to insert the flexible catheter 142 and introducer needle 134. For example, an angled needle in contact with the skin and driven horizontally can be used to enter the intradermal layer of the skin. Alternative methods of connecting the fluid connector to the base can be used to facilitate connecting and disconnecting of the fluid connector.

Although the exemplary embodiment described above is an insulin infusion set, it will be apparent to those of ordinary skill in the art that the principles of the present invention are also applicable to patch pumps (self-contained infusion devices with integral reservoirs and pumping mechanisms) and other types of medical infusion and injection devices.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. An infusion set, comprising:
   a base removably attached to a connector to form an enclosure;
   a flexible catheter movable from a first catheter position disposed substantially entirely within said enclosure to a second catheter position in which a free end of said catheter is disposed externally of said enclosure;
   an introducer needle located within said catheter and movable between a first introducer needle position disposed substantially entirely within said enclosure and a second introducer needle position in which a free end of said introducer needle is disposed externally of said enclosure; and
   an activation button movable by pressing between first, second and third button positions, wherein when said button is pressed from said first button position to said second button position, said catheter is moved from said first to said second catheter position, and said introducer needle is moved from said first to said second introducer needle position to facilitate insertion of said catheter, and when said button is pressed from said second button position to said third button position, said introducer needle is moved back toward said first introducer needle position with said free end of said catheter remaining disposed externally of said enclosure,
   wherein the activation button is pressed from the first button position to the second button position and to the third button position in a same direction toward a central axis of the infusion set, and said movement of said introducer needle is at an angle with respect to said movement of said activation button.

2. The infusion set in accordance with claim 1, wherein the connector is connectable to a medicament source.

3. An infusion set, comprising:
   a base removably attached to a connector to form an enclosure;
   a flexible catheter movable from a first catheter position disposed substantially entirely within said enclosure to a second catheter position in which a free end of said catheter is disposed externally of said enclosure;
   an introducer needle located within said catheter and movable between a first introducer needle position disposed substantially entirely within said enclosure and a second introducer needle position in which a free end of said introducer needle is disposed externally of said enclosure; and an activation button movable between first, second and third button positions, wherein when said button is moved from said first button position to said second button position, said catheter is moved from said first to said second catheter position, and said introducer needle is moved from said first to said second introducer needle position to facilitate insertion of said catheter, and when said button is moved from said second button position to said third button position, said introducer needle is moved back toward said first introducer needle position with said free end of said catheter remaining disposed externally of said enclosure, wherein the activation button moves from the first button position to the second button position and to the third button position in a same direction, and wherein said movement of said activation button is not in-line with said movement of said introducer needle;

the connector is connectable to a medicament source; and said connector has a penetrating member to pierce a septum in said base to create a fluid connection between said catheter and the medicament source when said connector is connected to said base.

4. The infusion set in accordance with claim 3, wherein tubing disposed in said base fluidly connects said penetrating member to said catheter.

5. The infusion set in accordance with claim 4, wherein said tubing moves with said introducer needle when said introducer needle moves between said first and second introducer needle positions.

6. The infusion set in accordance with claim 1, wherein said introducer needle and said catheter enter a skin surface at a non-perpendicular angle to the skin surface.

7. The infusion set in accordance with claim 6, wherein said angle is between approximately 30 and approximately 60 degrees, inclusive.

8. The infusion set in accordance with claim 6, wherein said angle is approximately 45 degrees.

9. An infusion set, comprising:

a base;

a catheter hub movable from a first catheter hub position to a second catheter hub position;

a flexible catheter connected to said catheter hub, said catheter being disposed substantially entirely within said base when said catheter hub is in said first catheter hub position and said catheter having a free end disposed externally of said base when said catheter hub is in said second catheter hub position;

an introducer hub movable between a first introducer hub position and a second introducer hub position;

an introducer needle located within said catheter and connected to said introducer hub, said introducer needle being disposed substantially entirely within said base when said introducer hub is in said first introducer hub position and said introducer needle having a free end disposed externally of said base when said introducer hub is in said second introducer hub position; and an activation button movable by pressing between first, second and third button positions, wherein when said button is pressed from said first button position to said second button position, said catheter hub is moved from said first catheter hub position to said second catheter hub position, and said introducer hub is moved from said first introducer hub position to said second introducer hub position, and when said activation button is pressed from said second button position to said third button position, said catheter hub is in said second catheter hub position and said introducer hub is moved back toward said first introducer hub position; wherein the activation button is pressed from the first button position to the second button position and to the third button position in a same direction toward a central axis of the infusion set, and said movement of said activation button is not in-line with said movement of said introducer needle.

10. The infusion set in accordance with claim 9, wherein a fluid connector is removably connected to said base and connectable to a medicament source.

11. The infusion set in accordance with claim 9, wherein a spring member biases said catheter hub toward said second catheter hub position.

12. The infusion set in accordance with claim 11, wherein a plurality of flexible members retain said catheter hub in said first catheter hub position.

13. The infusion set in accordance with claim 12, wherein a plurality of button arms extend outwardly therefrom to engage the plurality of flexible members to release said spring member.

14. The infusion set in accordance with claim 13, wherein said introducer hub is movably connected to said catheter hub to move from said first to said second introducer hub position.

15. The infusion set in accordance with claim 14, wherein a protrusion extending outwardly from said button engages said introducer hub to disconnect said introducer hub from said catheter hub and move said introducer hub back toward said first introducer hub position as said button moves from said second to said third button position.

16. The infusion set in accordance with claim 9, wherein said introducer needle and said catheter enter a skin surface at a non-perpendicular angle to the skin surface.

17. The infusion set in accordance with claim 16, wherein said angle is between approximately 30 and approximately 60 degrees, inclusive.

18. The infusion set in accordance with claim 16, wherein said angle is approximately 45 degrees.

19. The infusion set in accordance with claim 9, wherein a stop member is disposed in said base and abuts said catheter hub at said second catheter hub position.

20. A method of inserting a flexible catheter of an infusion set, comprising the steps of disposing the infusion set on a skin surface at an injection site;

depressing an activation button of the infusion set from a first button position to a second button position to expose a free end of an introducer needle and a free end of the flexible catheter;

inserting the introducer needle and the flexible catheter through the skin surface;

depressing the activation button of the infusion set from the second button position to a third button position to retract the free end of the introducer needle;

removing the inserted introducer needle from the skin surface; and storing the removed introducer needle substantially entirely within a body of the infusion set, wherein pushing the activation button from the first button position to the second button position and to the third button position occurs in a same direction toward a central axis of the infusion set; and movement of the introducer needle during at least one of the inserting, removing and storing steps occurs at an angle with respect to movement of the activation button.

21. The method of inserting a catheter of an infusion set in accordance with claim 20, further comprising
inserting the introducer needle and the catheter through the skin surface at an acute angle with respect to the skin surface.

22. The method of inserting a catheter of an infusion set in accordance with claim 20, wherein the catheter remains inserted through the skin surface after removing the introducer needle.

23. The infusion set in accordance with claim 3, wherein the movement of the activation button is not substantially parallel to the movement of the introducer needle.

* * * * *

UNITED STATES PATENT AND TRADEMARK OFFICE
CERTIFICATE OF CORRECTION

PATENT NO. : 10,434,285 B2
APPLICATION NO. : 13/984009
DATED : October 8, 2019
INVENTOR(S) : Ryan Schoonmaker and Cole Constantineau Page 1 of 1

It is certified that error appears in the above-identified patent and that said Letters Patent is hereby corrected as shown below:

In the Claims

In Claim 20, (Column 10, Line 64), "pushing" is corrected to read --depressing--.

Signed and Sealed this
Tenth Day of December, 2019

Andrei Iancu
*Director of the United States Patent and Trademark Office*